United States Patent
Hellstrand et al.

(10) Patent No.: US 6,613,788 B1
(45) Date of Patent: Sep. 2, 2003

(54) ELEVATION OF CIRCULATING BLOOD HISTAMINE LEVELS

(75) Inventors: Kristoffer Hellstrand, Göteborg (SE); Svante Hermodsson, Mölndal (SE); Kurt R. Gehlsen, Carlsbad, CA (US)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/526,816

(22) Filed: Mar. 15, 2000

Related U.S. Application Data

(63) Continuation of application No. 08/969,384, filed on Nov. 13, 1997, now Pat. No. 6,071,942, which is a continuation-in-part of application No. 08/767,338, filed on Dec. 16, 1996, now Pat. No. 6,221,893, which is a continuation-in-part of application No. 08/649,121, filed on May 14, 1996, now Pat. No. 5,961,969.

(51) Int. Cl.⁷ .................... A61K 9/70; A61K 31/415
(52) U.S. Cl. ......................... 514/396; 424/449
(58) Field of Search ................ 514/396; 424/449

(56) References Cited

U.S. PATENT DOCUMENTS

| | | |
|---|---|---|
| 5,348,739 A | 9/1994 | Hellstrand |
| 5,478,211 A | 12/1995 | Dominiak et al. |
| 5,843,979 A | * 12/1998 | Wille et al. ............. 514/408 |

FOREIGN PATENT DOCUMENTS

| | | |
|---|---|---|
| EP | 0 247 613 A2 | 12/1987 |
| EP | 0 483 759 A1 | 5/1992 |
| EP | 0 646 376 A1 | 8/1993 |
| JP | 7165582 | 6/1995 |
| WO | WO 91/04037 | 4/1991 |
| WO | WO 93/20803 | 10/1993 |
| WO | WO 93/24144 | 12/1993 |
| WO | WO 97/42968 | 11/1997 |

OTHER PUBLICATIONS

Facts and Compairsons, Jan., 1988. pp. 748a–748b.*
The Influence of Intraperitoneal Injections of Histamine on Tumour Growth in Fibrosarcoma–Bearing Mice, Burtin, et al., *Cancer Letters*, 12(3):195–201, Jan. 1981.
Successful Tumour Immunotherapy with Cimetidine in Mice, Osband, et al., *The Lancet*, No. 8221, 1:636–638, Mar. 21, 1981.
Factors Regulating Availability of Histamine at Tissue Receptors Ganellin and Parsons, eds., *Pharmacology of Histamine Receptors*, Beaven, Chapter Three, pp. 103–145, 8 1982.
Hydroxyl radical scavengers inhibit lymphocyte mitogenesis Novogrodsky, et al., *Proc. Natl. Acad. Sci. USA*, 79:1171–1174, Feb. 1982.
Suppression of Natural Killing in Vitro by Monocytes and Polymorphonuclear Leukocytes, Seaman, et al., *The Journal of Clinical Investigation*, 69:876–888, Apr. 1982.

The Differential Effects of Human Leukocytic Pyrogen/Lymphocyte–Activating Factor, T Cell Growth Factor, and Interferon on Human Natural Killer Activity, Dempsey, et al., *The Journal of Immunology*, May 17, 1982.
Tumor–Enhancing Effects of Cimetidine, Barna, et al., *Oncology*, 40:43–45, 1983.
Decreased blood histamine levels in patients with solid malignant tumors Burtin, et al., *Br. J. Cancer*, 47:367–372, 1983.
Combination of Cimetidine with other Drugs for Treatment of Cancer, Thornes, et al., *New England Journal of Medicine* 308:591–592, Mar. 10, 1983.
The Effect of Histamine, Antihistamines, and a Mast Cell Stabilizer on the Growth of Cloudman Melanoma Cells in DBA/2 Mice Nordlund, et al., *Journal of Investivative Dermatolog*, 81(1):28–31, Jul. 1983.
The Influence of Histamine on Immune and Inflammatory Responses, Beer, et al., *Advances in Immunology*, 35:209–268, 1984.
Hydroxyl radical scavengers inhibit human natural killer cell activity, Suthanthiran, et al., *Nature* 307:276–278, Jan. 1984.
Enhancement by serotonin of intra–tumour penetration of spleen cells, Lespinatas, et al., *Br. J. Cancer*, 50:545–547, Apr. 5, 1984.
Compared Mechanisms of Tumor Cytolysis by Human Natural Killer Cells and Activated Polymorphonuclear Leukocytes, Abrams, et al., *The Journal of Immunology* 132(6):3192–3196, Jun. 1984.
Down–Regulation of Human Natural Killer Activity Against Tumors by the Neutrophil Myeloperoxidase System and Hydrogen Peroxide, El–Hag, et al., *The Journal of Immunology* 133(6):3291–3297, Dec. 1984.
Effect of Ascorbic Acid on Human Natural Killer Cells, Huwyler, et al., *Immunology Letters*, 10:173–176, 1985.
The Role of Natural Killer Cells in the Control of Tumor Growth and Metastasis, Nabil Hanna, *Biochimica et Biophysica Acta*, 780:213–226, 1985.
Induction of Interferon–ã Production by Human Natural Killer Cells Stimulated by Hydrogen Peroxide, Munakata, et al., *The Journal of Immunology*, 134(4):2449–2455, Apr. 1985.

(List continued on next page.)

Primary Examiner—Theodore J. Criares
Assistant Examiner—Jennifer Kim
(74) *Attorney, Agent, or Firm*—Knobbe, Martens, Olson & Bear, LLP

(57) ABSTRACT

Methods for obtaining beneficial stable levels of circulating histamine are disclosed for use in methods for enhancing natural killer cell cytotoxicity and for elevating histamine levels in individuals in need thereof. In such methods, a beneficial level of circulating histamine is attained and an agent whose ability to enhance natural killer cell cytotoxicity is augmented by histamine is administered. Alternatively, stable beneficial levels of circulating histamine can be attained in subjects receiving chemotherapy or antiviral treatment. The invention may also be employed in treatments combining histamine, agents which enhance natural killer cell cytotoxicity, and chemotherapeutic agents. Optimization of the delivery of histamine and substances which induce the release of endogenous histamine are also disclosed.

22 Claims, 1 Drawing Sheet

OTHER PUBLICATIONS

Natural Killer Cell–Mediated Lysis Involves an Hydroxyl Radical–Dependent Step, Duwe, et al., *The Journal of Immunology*, 134(4):2637–2644, Apr. 1985.

Cytotoxicity by human adherent cells: oxygen–dependent and –independent cytotoxic reactions by different cell populations, Kessel, et al., *Immunology*, 58:291–296, 1986.

Histamine augments interleukin–2 production and the activation of cytotoxic T lymphocytes, Droege, et al., *Chemical Abstracts*, 104:No. 146898m, p. 146891, 1986.

Histamine Augments Interleukin–2 Production and the Activation of Cytotoxic T Lymphocytes, Dröge, et al., *Immunopharmacology*, 11:1–6, 1986.

Histamine Inhibits Interferon–ã Production via Suppression of Interleukin 2 Synthesis, Dohlsten, et al., *Cellular Immunology*, 101:493–501, 1986.

Histamine–Induced Suppressor Factor Inhibition of NK Cells: Reversal with Interferon and Interleukin 2, Nair, et al., *The Journal of Immunology*, 136(7):2456–2462, Apr. 1, 1986.

Hydeoperoxide Metabolism in Cyanobacteria, Tel–Or, et al., *Archives of Biochemistry and Biophysics*, 246(1):396–402, Apr. 1986.

Histamine $H_2$–Receptor–Mediated Regulation of Human Natural Killer Cell Activity, Hellstrand, et al., *The Journal of Immunology*, 137(2):656–660, Jul. 15, 1986.

Biogenic Amines in the Regulation of Human Natural Killer Cell Cytotoxicity (Thesis), Hellstrand, *Medi Press, Göteborg, Sweden*, 1987.

Differential Effects of Histamine Receptor Antagonists on Human Natural Killer Cell Activity, Hellstrand, et al., *Int. Archs Allergy appl. Immunology*, 84:247–255, 1987.

Selective, Histamine–Mediated Immunosuppression in Laryngeal Cancer, Richtsmeier, et al., *Ann Otol Rhinol Laryngol*, 96(5):569–572, 1987.

Thyroid Hermone Regulates TRH Biosysnthesis in the Paraventricular Necleus of the Rat Hypothalamus Segerson, et al., *Science*, 238:78–80.

A Progress Report on the Treatment of 157 Patients With Advanced Cancer Using Lymphokine–Activated Killer Cells and Interleukin–2 or High–Dose Interleukin–2 Alone Rosenberg, et al., *N. Eng. Journal of Medicine*, 316(15):889–897, Apr. 9, 1987.

Clinical Improvement in Advanced Cancer Disease After Treatment Combining Histamine and H2–Antihistaminics (Ranitidine or Cimetidine), Burtin, et al., *Eur. Journal of Cancer Clin. Oncol.*, 24(2):161–167, 1988 (Accepted Jun. 1987).

Identification of Cellular Mechanisms Operational In Vivo During the Regression of Established Pulomonary Metastases by the Systemic Administration of High–Dose Recombinant Interleukin 2 Mulú, et al., *Journal of Immunology*, 139(1):285–294, Jul. 1987.

Role of Serotonin in the Regulation of Human Natural Killer Cell Cytotoxicity, Hellstrand, et al., *The Journal of Immunology*, 139(2):869–875, Aug. 1, 1987.

The IL–2 Receptor â Chain (p70): Role in Mediating Signals for LAK, NK, and Proliferative Activities, Siegel, et al., *Science*, vol. 238, Oct. 2, 1987.

Chondrocyte Antioxidant Defenses: The Roles of Catalase and Glutathione Peroxidase in Protection Against $H_2O_2$ Dependent Inhibition of Proteoglycan Biosynthesis, Baker, et al., *The Journal of Rheumatology*, 15(4):670–677, 1988.

Clinical Improvement in Advanced Cancer Disease After Treatement Combining Histamine and H2–Antihistaminics (Rantidine or Cimetidine) Burtin, et al., *Eur. J. Clin. Oncol.*, 24(2):161–167, 1988.

Antioxidants Inhibit Proliferation and Cell Surface Expression of Receptors for Interleukin–2 and Transferrin in T Lymphocytes Stimulated with Phorbol Myristate Acetate and Ionomycin Chaudhri, et al., *Cellular Immunology*, 115:204–213, 1988.

Role of Flavonoids in the Oxygen–Free Radical Modulation of the Immune Response, Pignol, et al., *Plant Flavonoids in Biology & Medicine II: Biochemical, Cellular . . .*, 173–182, 1988.

Flavone–8–Acetic Acid Augments Systemic Natural Killer Cell Activity and Synergizes with IL–2 for Treatment of Murine Renal Cancer, Wiltrout, et al., *The Journal of Immunology*, 140(9):3261–3265, May 1, 1988.

Interleukin–2: Inception, Impact, and Implications, Smith, Kendall A., *Science*, 240:1169–1176, May 27, 1988.

Enhancement of Natural Killer Activity in Human Peripheral Blood by Flavone Acetic Acid, Urba, et al., *The Journal of the National Cancer Institute*, 80(7):521–525, Jun. 1, 1988.

The Development of New Immunotherapies for the Treatment of Cancer Using Interleukin–2, Rosenberg, *Annals of Surgery*, 208(2):121–135, Aug. 1988.

Interleukin 2 as a Pharmacologic Reagent, Lotze, eds., *National Institutes of Health*, Smith, Chapter 12, pp. 237–245, Oct. 28, 1988.

Augmentation of Natural Killer Activity, Induction of IFN and Development Tumor Immunity During the Successful Treatment or Established Murine Renal Cancer Using Flavone Acetic Acid and IL–2, Hornung, et al., *The Journal of Immunology*, 141(10):3671–3679, Nov. 15, 1988.

Enhancement of Human Natural Killer Cell Function by the Combined Effects of Tumor Necrosis Factor á or Interleukin–1 and Interferon–á or Interleukin–2, Østensen, et al., *Journal of Biological Response Modifiers*, 8:53–61, 1989.

Interleukin–2 can induce suppression of human natural killer cell cytotoxicity, Hellstrand, et al., *Clin. Exp. Immunol*, 77(3):410–416, 1989.

Biology of Natural Killer Cells Trinchieri, *Advances in Immunology*, 47:187–376, Accepted for Publication Jan. 23, 1989.

A Phase II Study of Interleukin–2 and Lymphokine–Activated Killer Cells in Patients with Metastatic Malignant Melanoma Dutcher, et al., *Journal of Clinical Oncology*, 7(4):477–485, Apr. 1989.

Comparative Effect of Recombinant IL–1, –2, –3, –4, and –6, IFN–ã, Granulocyte–Macrophage–Colony–Stimulating Factor, Tumor Necrosis Factor–á, and Histamine–Releasing Factors on the Secretion of Histamine From Basophils, Alam, et al., *The Journal of Immunology*, 142(10):3431–3435, May 18, 1989.

Activation of Natural Killer Cells via the p75 Interleukin 2 Receptor, Phillips, et al., *J. Exp. Med.*, 170:291–296, Jul. 1989.

Inhibition of Lymphokine–Activated Killer– and Natural Killer–Mediated Cytotoxicities by Neutrophils, Shau, et al., *The Journal of Immunology*, 143(3):1066–1072, Aug. 1989.

Regulation of Human Basophil Mediator Release by Cytokines, Schleimer, et al., *The Journal of Immunology*, 143(4):1310–1317, Aug. 15, 1989.

Inhibition of Lymphokine–activated Killer Cell Function by Human Alveolar Macrophages, Roth, et al., *Cancer Research*, 49:4690–4695, Sep. 1989.

A Cell–To–Cell Mediated Interaction Involving Monocytes and Non–T/CD16+ Natural Killer (NK) Cells is Required for Histamine $H_2$–Receptor–Mediated NK–Cell Activation, Hellstrand, et al., *Scand J. Immuno*, 31:631–644, 1990.

Deficiency in Catalase Activity Correlates with the Appearance of Tumor Phenotype in Human Keratinocytes, Rabilloud, et al., *Int. J. Cancer*, 45:952–956, 1990.

Enhancement of Human Natural Killer Cell Cytotoxicity by Serotonin: Role of Non–T/CD16+ NK Cells, Accessory Monocytes, and 5–$HT_{1A}$ Receptors, Hellstrand, et al., *Cellular Immunology*, 127:199–214, 1990.

Flavone acetic acid antitumour activity against a mouse pancreatic adenocarcinoma is mediated by natural killer cells, Damia, et al., *Cancer Immunol Immunother*, 32:241–244, 1990.

Monocyte–Mediated Suppresion of IL–2–Induced NK–Cell Activation, Hellstrand, et al., *Scand. J. Immunol*, 32(2):183–192, 1990.

Possible involvement of adenosine 3':5'–cyclic monophosphate and extracellular calcium ions in histamine stimulation of interleukin–1 release from macrophage–like P388D1 cells, Okamoto, et al., *Immunology*, 70:186–190, 1990.

Synergistic Activation of Human Natural Killer Cell Cytotoxicity by Histamine and Interleukin–2, Hellstrand, et al., *Int. Arch. Allergy Appl. Immunolog*, 92:379–389, 1990.

Histamine Type 2–Receptor Antagonists and Cancer Immunotherapy, Tom Smith, MD, *Comprehensive Therapy*, 16(1):8–13, 1990.

Splenic Versus Hepatic Artery Infusion of Interleukin–2 in Patients with Liver Metastases, Mavligit, et al., *Journal of Clinical Oncology*, 8(2):319–324, 1990.

Renal Cell Carcinoma: Treatment With Recombinant Interleukin–2 Plus Beta–Interferon, Krigel, et al., *Journal of Clinical Oncology*, 8(3):460–467, Mar. 1990.

High–Dose Recombinant Interleukin–2 Alone: A Regimen With Limited Activity in the Treatment of Advanced Renal Cell Carcinoma, Abrams, et al., *Journal of the National Cancer Institute*, 82(14):1202–1206, Jul. 18, 1990.

Recombinant Interleukin–2 and Adoptive Immunotherapy Alternated with Dacarbazine Therapy in Melanoma: A National Biotherapy Study Group Trial, Dilman, et al., *Journal of the National Cancer Institute*, 82(16):1345–1348, Aug. 15, 1990.

Immunological Effects of Flavone Acetic Acid, Triozzi, et al., *Cancer Research*, 50:6483–6485, Oct. 15, 1990.

Role of Histamine in Natural Killer Cell–Mediated Resistance Against Tumor Cells, Hellstrand, et al., *The Journal of Immunology*, 145(12):4366–4370, Dec. 15, 1990.

Treatment of acute myeloid leukaemia patients with recombinant interleukin 2: a pilot study Foa, et al., *British Journal of Haematology*, 77:491–496, 1991.

Cell–to–Cell Mediated Inhibition of Natural Killer Cell Proliferation by Monocytes and its Regulation by Histamine $H_2$–Receptors, Hellstrand, et al., *Scand J.Immunol*, 34:741–752, 1991.

Induction of Natural Killer Activity by Xanthenone Analogues of Flavone Acetic Acid: Relation with Antitumour Activity, Ching, et al., *Eur. J. Cancer*, 27(1):79–83, 1991.

In vitro Methods for Screening Agents with an Indirect Mechanism of Antitumour Activity: Xanthenone Analogues of Flavone Acetic Acid, Ching, et al., *Eur. J. Cancer*, 27(12):1684–1689, 1991.

Monocyte–Induced Down–Modulation of CD16 and CD56 Antigens on Human Natural Killer Cells and its Regulation by Histamine $H_2$–Receptors, Hellstrand, et al., *Cellular Immunology*, 138:44–45, 1991.

Natural killer (NK) and lymphokine activated killer (LAK) cell activity in patients (PTS) treated with Flavone acetic acid (FAA), Galligioni, *Annals of Oncology*, 2:145–150, 1991.

Production of Large Amounts of Hydrogen Peroxide by Human Tumor Cells, Szatrowski, et al., *Cancer Research*, 51:794–798, Feb. 1991.

A Phase II Study of High–Dose Continuous Infusion Interleukin–2 With Lymphokine–Activated Killer Cells in Patients With Metastatic Melanoma, Dutcher, et al., *Journal of Clinical Oncology*, 9(4):641–648, Apr. 1991.

Continuous Interleukin–2 and Lymphokine–Activated Killer Cells for Advanced Cancer: A National Biotherapy Study Group Trial, Dillman, et al., *Journal of Clinical Oncology*, 9(7):1233–1240, Jul. 1991.

Sequential Administration of Recombinant Human Interleukin–2 and Dacarbazine in Metastatic Melanoma: A Multicenter Phase II Study, Stoter, et al., *Journal of Clinical Oncology*, 9(9):1687–1691, Sep. 1991.

Interactions between human monocytes and tumor cells. Monocytes can either enhance or inhibit the growth and survival of K562 Cells, Davies, et al., Nov. 1991.

Effects of Flavonoids on Immune and Inflammatory Cell Functions, Middleton, et al., *Biochemical Pharmacology*, 43(6):1167–1179, 1992.

Immunotherapy of mammary adenocarcinoma metastases in C3H/HeN mice with chronic administration of cyclo–oxygenase inhibitors alone or in combination with IL–2, Khoo, et al.,*Clin. Exp. Metastasis*, 10(4):239–252, 1992.

Oxygen Free Radical Generation and Regulation of Proliferative Activity of Human Mononuclear Cells Responding to Different Mitogens, Whitacre, et al., *Cellular Immunology*, 144:287–295, 1992.

A phase II study of interleukin–2 and interferon–alpha in head and neck cancer, Schantz, et al., *Investigational New Drugs*, 10:217–223, 1992.

Regulation of the Natural Killer Cell Response to Interferon–á by Biogenic Amines, Hellstrand, et al., *Journal of Interferon Research*, 12:199–206, 1992.

A Randomized Phase II Trial of Continuous Infusion Interleukin–2 or Bolus Injection Interleukin–2 Plus Lymphokine–Activated Killer Cells for Advanced Renal Cell Carcinoma, Weiss, et al., *Journal of Clinical Oncology*, 10(2):275–281, Feb. 1992.

Natural Killer (NK) Cell Stimulatory Factor Increases the Cytotoxic Activity of NK Cells from Both Healthy Donors and Human Immunodeficiency Virus–infected Patients, Chehimi, et al., *Journal of Experimental Medicine*, 175:789–796, Mar. 1992.

Chemoimmunotherapy of Metastatic Murine Renal Cell Carcinoma Using Flavone Acetic Acid and Interleukin 2, Salup, et al., *The Journal of Urology*, 147:1120–1123, Apr. 1992.

Phase I Trial of High–Dose Bolus Interleukin–2 and Interferon Alfa–2a in Patients With Metastatic Malignancy, Budd, et al., *Journal of Clinical Oncology*, 10(5):804–809, May 1992.

Prolonged Continuous Intravenous Infusion Interleukin–2 and Lymphokine–Activated Killer–Cell Therapy for Metastatic Renal Cell Carcinoma, Thompson, et al., *Journal of Clinical Oncology*, 10(6):960–968, Jun. 1992.

Phase II Study of Subcutaneous Interleukin–2 in Unselected Patients With Advanced Renal Cell Cancer on an Outpatient Basis, Sleijfer, et al., *Journal of Clinical Oncology*, 10(7):1119–1123, Jul. 1992.

A Phase II Trial of Interleukin–2 and Interferon Alfa–2a in Patients With Advanced Renal Cell Carcinoma, Ilson, et al., *Journal of Clinical Oncology*, 10(7):1124–1130, Jul. 1992.

Effect of indomethacin plus ranitidine in advanced melanoma patients on high–dose interleukin–2 Mertens, et al., *The Lancet*, 340:397–398, Aug. 15, 1992.

Effects of Cancer Immunotherapy with Indomethacin and Interleukin–2 on Murine Hemopoietic Stem Cells, Saarloos, et al., *Cancer Research*, 52:6465–6462, Dec. 1, 1992.

Effects of histamine type–2 receptor antagonists on indomethacin and IL–2 immunotherapy of metastasis, Saarloos, et al., *Clin. Exp. Metastasis*, 11(3):275–283, 1993.

Serotonergic 5–HT$_{1A}$ Receptors Regulate a Cell Contact–Mediated Interaction between Natural Killer Cells and Monocytes, Hellstrand, et al., *Scand J. Immunol*, 37:7–18, 1993.

Sustained Indomethacin and Ranitidine with Intermittent Continuous Infusion Interleukin–2 in Advanced Malignant Melanoma: A Phase II Study, Mertens, et al., *Clinical Oncology*, 5(2):107–113, 1993.

Selective Modulation of Human Natural Killer Cells In Vivo After Prolonged Infusion of Low Dose Recombinant Interleukin 2 Caligiuri, et al., *J. Clin. Invest.*, 91:123–132, Jan. 1993.

Effect of Reactive Oxygen Intermediates and Antioxidants on Proliferation and Function of T Lymphocytes Dröge, et al., *Methods in Enzymology*, 234:135–151, 1994.

Histamine in immunotherapy of advanced melanoma: a pilot study Hellstrand, et al., *Cancer Immunol. Immunother*, 39:416–419, 1994.

Histaminergic regulation of antibody–dependent cellular cytotoxicity of granulocytes, monocytes, and natural killer cells Hellstrand, et al., *Journal of Leukocyte Biology*, 55:392–397, Mar. 1994.

Phase II Study of Subcutaneous rHu Interleukin–2 in Patients with Acute Myelogenous Leukemia in Partial or Complete Second Remission and Partial Relapse Shepherd, et al., *British Journal of Haematology*, Supp. 1, 87:205, Jun. 1994.

Hydrogen peroxide as a potent activator of T lymphocyte functions Los, et al., *Eur. Journal of Immunology*, 25:159–165, 1995.

Histaminergic Regulation of NK Cells Hellstrand, et al., *Journal of Immunology*, 153(11):4940–4947, Dec. 1, 1994.

Remission maintenance therapy with histamine and interleukin–2 in acute myelogenous leukaemia Brune, et al., *British Journal of Haematlogy*, 92:620–626, 1996.

Histamine and Immune Responses Plaut, et al., *Pharmacology of Histamine Receptors*, Publication No. 454, pp. 392–435.

Induction of lymphokine activated killer cells in serum–free medium Froelich, et al., *Journal of Immunological Methods*, 86(2):205–211, (1986).

Peptide derivative cytochrome inhibit enzyme system oxidation burst phagocyte cell inflammation disease Malech, et al., Database WPI/Derwent (Abstract), Jul. 25, 1989.

Effects of Histamine on IgG3 Monoclonal Antibody Directed Effector Cell Lysis of Tumor Cells Welt, et al., *Proceedings of ASCO*, 7:164, Abstract 632, Mar. 1988.

Role of Histamine in Natural Killer Cell–Dependent Protection Against Herpes Simplex Virus Type 2 Infection in Mice Hellstrand, et al., *Clinical and Diagnostic Laboratory Immunology*, 2(3):277–280, May 1995.

Abstract XP 002036365 "Enhance Agent Immuno Carcinostatic Agent Compose Sugar Protein Immuno Carcinostatic Active Contain Histamine Acid Adduct Salt Histamine".

\* cited by examiner

ELEVATION OF CIRCULATING BLOOD HISTAMINE LEVELS

CROSS-REFERENCE TO RELATED APPLICATIONS

This application is a continuation of U.S. patent application Ser. No. 08/969,384, filed Nov. 13, 1997 now 6,071,942 which is a continuation-in-part of U.S. patent application Ser. No. 08/767,338, filed Dec. 16, 1996, now U.S. Pat. No. 6,221,8293 which is a continuation-in-part of U.S. patent application Ser. No. 08/649,121, filed May 14, 1996, now U.S. Pat. No. 5,961,969.

BACKGROUND OF THE INVENTION

The present invention relates to methods of treating cancer or infectious disease in which histamine is administered in conjunction with additional agents. The additional agent may be an agent which stimulates the proliferative and/or cytotoxic activity of natural killer (NK) cells and cytotoxic T lymphocytes (CTLs) in a synergistic fashion with histamine. Alternatively, the additional agent may be a chemotherapeutic, antiviral, vaccine or antibiotic agent. Methods combining histamine, agents which act synergistically with histamine to enhance the cytotoxicity of NK cells and CTLs, and chemotherapeutic agents are also contemplated.

The invention also relates to a method of elevating circulating blood histamine levels for prolonged periods of time in individuals with decreased circulating histamine levels. Such decreased levels may be due to cancer, viruses or other infectious agents or pathological situations.

The invention is based on the surprising observation that despite previous reports of histamine's short half life in the body, it is possible to attain stable beneficial levels of circulating blood histamine and to maintain these beneficial levels for hours or days after the last administration of histamine. This observation facilitates treatments in which histamine administration to obtain beneficial levels of circulating blood histamine is combined with treatment with other agents. The invention also relates to improvements in the method of administering histamine. A brief review of the observations leading to the present invention is provided below to place the present invention in context.

A. Cell Types Involved in the Generation of an Immune Response

Recent anticancer and antiviral strategies have focussed on utilizing the host immune system as a means of cancer or antiviral treatment or therapy. The immune system has evolved complex mechanisms for recognizing and destroying foreign cells or organisms present in the body of the host. Harnessing the body's immune mechanisms is an attractive approach to achieving effective treatment of malignancies and viral infections.

A wide array of effector cells, each having its own characteristics and role, implement the immune response. One type of effector cell, the B cell, generates antibodies targeted against foreign antigens encountered by the host. In combination with the complement system, antibodies direct the destruction of cells or organisms bearing the targeted antigen.

Another type of effector cell, the T cell, is divided into subcategories which play different roles in the immune response. Helper T cells secrete cytokines which stimulate the proliferation of other cells necessary for mounting an effective immune response, while suppressor T cells down regulate the immune response. A third category of T cell, the cytotoxic T cell (CTL), is capable of directly lysing a targeted cell presenting a foreign antigen on its surface.

An additional type of effector cell is the natural killer cell (NK cell), a type of lymphocyte having the capacity to spontaneously recognize and destroy virally infected cells and a variety of malignant cell types. This characteristic of NK cells makes them an attractive candidate for exploitation in anticancer and antiviral treatments and therapies based on using the host's immune system as a weapon against malignant tumors and viruses.

B. Cytokines Involved in Mediating the Immune Response

The interplay between the various effector cells listed above is influenced by the activities of a wide variety of chemical factors which serve to enhance or reduce the immune response as needed. Such chemical modulators may be produced by the effector cells themselves and may influence the activity of immune cells of the same or different type as the factor producing cell.

One category of chemical mediators of the immune response is cytokines, molecules which stimulate a proliferative response in the cellular components of the immune system.

Interleukin-2 (IL-2) is a cytokine synthesized by T cells which was first identified in conjunction with its role in the expansion of T cells in response to an antigen (Smith, K.A. Science 240:1169 (1988). It is well known that IL-2 secretion is necessary for the full development of cytotoxic effector T cells (CTLs), which play an important role in the host defense against viruses. Several studies have also demonstrated that IL-2 has antitumor effects that make it an attractive agent for treating malignancies (see e.g. Lotze, M.T. et al, in "Interleukin 2", ed. K.A. Smith, Academic Press, Inc., San Diego, Calif., p. 237 (1988); Rosenberg, S., Ann. Surgery 208:121 (1988)). In fact, IL-2 has been utilized to treat subjects suffering from malignant melanoma, renal cell carcinoma, and acute myelogenous leukemia. (Rosenberg, S.A. et al., N. Engl. J. Med. 316:889–897 (1978); Bukowski, R. M. et al., J. Cliin. Oncol. 7:477–485 (1989); Foa, R. et al., Br. J. Haematol. 77:491–496 (1990)).

It appears likely that NK cells are responsible for the anti-tumor effects of IL-2. For example, IL-2 rapidly and effectively augments the cytotoxicity of isolated human NK cells in vitro (Dempsey, R.A., et al., J. Immunol. 129:2504 (1982); Phillips, J. H., et al. J. Exp. Med. 170:291 (1989)). Thus, the cytotoxic activity of NK cells treated with IL-2 is greater than the constitutive levels of cytotoxicity observed in untreated cells. Furthermore, depletion of NK-cells from animals eliminates IL-2's antitumor effects. (Mule, J. J. et al, J. Immunol. Invest. 139:285 (1987); Lotze, M.T. et al., supra). Additional evidence for the role of NK cells results from the observation that NK cells are the only resting human peripheral blood lymphocytes expressing the IL-2 receptor on their cell surface. (Caliguri, M. A. et al., J. Clin. Invest. 91:123–132 (1993)).

Another cytokine with promise as an anti-cancer and antiviral agent is interferon-α. Interferon-a (IFN-α) has been employed to treat leukemias, myeloma, and renal cell carcinomas. Isolated NK cells exhibit enhanced cytotoxicity in the presence of IFN-α. Thus, like IL-2, IFN-α also acts to augment NK cell mediated cytotoxicity. (Trinchieri, G. Adv. Immunol. 47:187–376 (1989)).

C. In vivo Results of Histamine and Histamine Agonist Treatments

Histamine is a biogenic amine, i.e. an amino acid that possesses biological activity mediated by pharmacological receptors after decarboxylation. The role of histamine in immediate type hypersensitivity is well established. (Plaut, M. and Lichtenstein, L. M. 1982 Histamine and immune responses. In *Pharmacology of Histamine Receptors*, Ganellin, C. R. and M. E. Parsons eds. John Wright & Sons, Bristol pp. 392–435.) Examinations of whether histamine or histamine antagonists can be applied to the treatment of cancer have yielded contradictory results. Some reports suggest that administration of histamine alone suppressed tumor growth in hosts having a malignancy. (Burtin, Cancer Lett. 12:195 (1981)). On the other hand, histamine has been reported to accelerate tumor growth in rodents (Nordlund, J. J. et al., J. Invest. Dermatol. 81:28 (1983)).

Similarly, contradictory results were obtained when the effects of histamine receptor antagonists were evaluated. Some studies report that histamine receptor antagonists suppress tumor development in rodents and humans (Osband, M.E. et al., Lancet 1 (8221):636 (1981)). Other studies report that such treatment enhances tumor growth and may even induce tumors (Bama, B.P. et al., Oncology 40:43 (1983)).

D. Synergistic Effects of Histamine and IL-2

Despite the conflicting results when histamine is administered alone, recent reports clearly reveal that histamine acts synergistically with cytokines to augment the cytotoxicity of NK cells and CTLs. Thus, therapies employing the combination of histamine and cytokines represent an attractive approach to anti-cancer strategies based on using the host immune system to attack the malignancy. Similarly, antiviral treatments using any of the well known antiviral agents is also contemplated.

Studies using histamine analogues suggest that histamine's synergistic effects are exerted through the $H_2$-receptors expressed on the cell surface of phagocytic cells such as monocytes, macrophages and granuylocytes. For example, the $H_2$-receptor agonist dimaprit was capable of augmenting NK cell mediated cytotoxicity, while close structural analogues lacking biological activity failed to produce an effect. Additionally, $H_2$-receptor antagonists blocked the effects of histamine and dimaprit, implicating the $H_2$-receptor in the transduction of the histamine response. (Hellstrand, K. et al., J. Immunol. 137:656 (1986)).

Histamine's synergistic effect when combined with cytokines is not the result of a direct positive effect of histamine on NK cell and CTL cytotoxicity. Rather, the synergistic effects result from the suppression of a down regulation of cytotoxicity mediated by other cell types present along with the cytotoxic cells. The discussion below provides some of the evidence suggesting that histamine's synergistic effects result from the suppression of negative signals exerted by other cell types.

U.S. Pat. No. 5,348,739, which is incorporated herein by reference, discloses the synergistic effects of histamine and interleukin-2. As discussed above, IL-2 normally induces a cytotoxic response in NK cells. In vitro studies with NK cells alone confirm that cytotoxicity is stimulated when IL-2 is administered. However, in the presence of monocytes, the IL-2 induced enhancement of cytotoxicity of NK cells is suppressed.

In the absence of monocytes, histamine had no effect or weakly suppressed NK mediated cytotoxicity. (U.S. Pat. No. 5,348,739; Hellstrand, K. et al., J. Immunol. 137:656 (1986); Hellstrand, K. and Hermodsson, S., Int. Arch. Allergy Appl. Immunol. 92:379–389 (1990)). However, NK cells exposed to histamine and IL-2 in the presence of monocytes exhibit elevated levels of cytotoxicity relative to that obtained when NK cells are exposed only to IL-2 in the presence of monocytes. Id. Thus, the synergistic enhancement of NK cell cytotoxicity by combined histamine and interleukin-2 treatment results not from the direct action of histamine on NK cells but rather from suppression of an inhibitory signal generated by monocytes.

Without being limited to a particular mechanism, it is believed that the inhibitory effects of monocytes on cytotoxic effector cells such as NK cells and CTLs result from the generation of $H_2O_2$ by monocytes. It has been reported that the production of $H_2O_2$ by monocytes suppresses NK cell cytotoxicity. (Van Kessel, K. P. M. et al., Immunology, 58:291–296 (1986); El-Hag, A. and Clark, R. A. J. Inimunol. 133:3291–3297 (1984); Seaman, W. E. et al., J. Clin. Invest. 69:876–888(1982)). Further evidence of the role of $H_2O_2$ in suppressing NK cell cytotoxicity comes from in vitro studies showing that the addition of catalase, an enzyme which acts to remove $H_2O_2$, to preparations of monocytes and NK cells exposed to IL-2 removes the inhibitory effects of the monocytes. (Seaman, supra.) Thus, histamine may exert its synergistic effects by reducing the level of $H_2O_2$ produced by monocytes. Hellstrand, K., Asea, A., Hermnodsson, S. Histaminergic regulation of antibody-dependent cellular cytotoxicity of granulocytes, monocytes and natural killer cells, J. Leukoc. Biol. 55:392–397 (1994).

Monocytes are not the only cell type which negatively regulates NK cell and CTL cytotoxicity. Experiments have demonstrated that granulocytes suppress both the constitutive and IL-2 induced cytotoxic activity of NK cells in vitro. Like the monocyte mediated suppression discussed above, granulocyte mediated suppression is synergistically overcome by treatment with IL-2 and histamine. (U.S. Pat. No. 5,348,739; Hellstrand, K., Asea, A., Hermodsson, S. Histaminergic regulation of antibody-dependent cellular cytotoxicity of granulocytes, monocytes and natural killer cells, J. Leukoc. Biol. 55:392–397 (1994)).

It appears that the $H_2$-receptor is involved in transducing histamine's synergistic effects on overcoming granulocyte mediated suppression. For example, the effect of histamine on granulocyte mediated suppression of antibody dependent cytotoxicity of NK cells was blocked by the $H_2$-receptor antagonist ranitidine and mimicked by the $H_2$ receptor agonist dimaprit. In contrast to the complete or nearly complete abrogation of monocyte mediated NK cell suppression by histamine and IL-2, such treatment only partially removed granulocyte mediated NK cell suppression. (U.S. Pat. No. 5,348,739; Hellstrand, K. et al., Histaminergic regulation of antibody dependent cellular cytotoxicity of granulocytes, monocytes and natural killer cells., J. Leukoc. Biol 55:392–397 (1994)).

As suggested by the experiments above, therapies employing histamine and cytokines are effective anti-cancer strategies. U.S. Pat. No. 5,348,739 discloses that mice given histamine and IL-2 prior to inoculation with melanoma cell lines were protected against the development of lung metastatic foci. This effect was a consequence of synergistic interaction between histamine and IL-2, as demonstrated by the significant reduction in metastatic foci observed in mice given histamine and IL-2 as compared to mice given histamine or IL-2 alone.

In addition to the synergistic effects observed in the assay of lung metastatic foci, synergistic effects of histamine plus IL-2 treatment were also observed in assays in which NK cell cytotoxicity was measured by determining the ability of mice to kill malignant cell lines derived from both humans and mice which were injected into them. Id.

In studies conducted to investigate the role of histamine in NK-cell dependent protection against herpes simplex virus (HSV) type 2, it was discovered that a single dose of histamine could prolong survival time in animals inoculated intravenously with HSV, and a synergistic effect on the survival time of animals treated with a combination of histamine and IL-2 was observed (Hellstrand, K. et al., Role of histamine in natural killer cell-dependent protection against herpes simplex virus type 2 infection in mice., Clin. Diagn. Lab. Immunol. 2:277–280 (1995)).

The above results demonstrate that strategies employing a combination of histamine and IL-2 are an effective means of treating malignancies and viral infection.

E. Synergistic Effects of Histamine and Interferon-α

Histamine also acts synergistically with interferon-α to overcome the suppression of NK cell cytotoxicity by monocytes (Hellstrand et al., Regulation of the NK cell response to interferon-alpha by biogenic amines, J. Interferon Res. 12:199–206 (1992)). Like IL-2, interferon-α augments NK cell constitutive NK cell cytotoxicity. Id. Monocytes suppress the interferon-α mediated enhancement of NK cell killing of malignant target cells in vitro. Monocyte mediated suppression of NK cell cytotoxicity was overcome by treatment with histamine and interferon-α. The effects of histamine were blocked by $H_2$-receptor antagonists and mimicked by $H_2$-receptor agonists. Compounds bearing structural similarity to the $H_2$-receptor agonist dimaprit but lacking the activity of the agonist were unable to act synergistically with interferon-α. (Hellstrand et al. J., Interferon Res. 12:199–206 (1992)).

F. Human Treatments Combining Histamine, Interleukin-2 and Interferon-α

The in vitro and animal results discussed above suggested that histamine+IL-2+interferon-α was a promising method for treating human malignancies. In fact, combined histamine, IL-2, and interferon-α treatments have proven effective in the treatment of a variety of human malignancies, providing a 75% response rate significantly greater than that observed with IL-2 alone. (Hellstrand et al., Histamine in Immunotherapy of Advanced Melanoma: A Pilot Study, Cancer Immunology and Immunotherapy 39: 416–419 (1994)). In the above study, subjects received a constant infusion of IL-2 (Proleukin®, Eurocetus), $18 \times 10^6$ U/m² on days 1–5 and 8–12, repeated every 4–6 weeks, as well as interferon-α ($6 \times 10^6$ U daily, s.c.). In addition to the IL-2, eight of the subjects received histamine dihydrochloride (1 mg s.c.) twice daily. Id.

Only one subject in the group receiving IL-2 and interferon-α exhibited a partial or mixed response, a response rate of 14% (1 of 7). In contrast, the group receiving both IL-2, interferon-α and histamine showed an corresponding response rate of 75% (6 of 8). Only two of these subjects failed to respond. Id.

Thus, histamine+IL-2+interferon-α is an effective anti-cancer therapy.

G. Human Treatments with Histamine +IL-2+ Chemotherapeutic Agents

Recently, the efficacy of treatments employing histamine, IL-2, and chemotherapeutic agents was examined in humans suffering from acute myelogenous leukemia (AML). (Brune and Hellstrand, Remission Maintenance Therapy with Histamine and Interleukin-2 in Acute Myelogenous Leukemia, Br. J. Haematology, March 1996).

In one set of experiments, killing of AML blasts by NK cells was examined in vitro. IL-2 induced NK mediated cytotoxicity, but this effect was suppressed by monocytes. Histamine did not affect the IL-2 induced cytotoxic response in the absence of monocytes but blocked the suppressive effects of the monocytes. However, in the presence of the $H_2$-receptor antagonist ranitidine, histamine was ineffective in overcoming the monocyte suppression. Id.

Additionally, AML patients in remission were treated with histamine+IL-2+the chemotherapeutic agents cytarabine and thioguanine and the duration of remission was measured and compared to the length of remissions prior to initiating the treatment. Five of the patients receiving histamine+IL-2+cytarabine+thioguanine remained in complete remission ranging in duration from 9–27 months at the time of publication. Two patients relapsed after remissions lasting 8 and 33 months. In the five patients who had undergone a remission followed by a relapse prior to initiation of the histamine+IL-2+cytarabine+thioguanine regimen, the duration of remissions following initiation of the regimen exceeded the duration of the prior remission. Id. Such "inversion of remission time" is rare in the natural course of AML and reportedly only occurs in a small fraction (<10%) of AML patients treated with IL-2 as the single agent. Shepherd et al, Phase II Study of Subcutaneous rHU IL-2 in Patients with Acute Myelogenous Leukernia in Partial or Complete Second Remission and Partial Relapse, Br. J. Haematol. S87, 205 (1994).

Thus, histamine+IL-2+chemotherapeutic agents is an effective anti-cancer therapy.

H. Optimization of Histamine Delivery

Histamine is a strongly bioactive molecule with powerful biological effects. We have discovered that bolus doses of effective amounts of histamine have significant unwanted side effects, including flushing, discomfort, increased heart and respiratory rate, hypotension, and severe headache. At the same time, we have discovered that histamine-mediated therapy is most effective if provided in discrete dosages over a relatively short time period as opposed to infusion or controlled release over a period of days or weeks.

SUMMARY OF THE INVENTION

One embodiment of the present invention is a method for treating a histamine-deficient individual, comprising the steps of: identifying an individual in need of enhanced circulating blood histamine levels; and administering to the individual an effective amount of a pharmaceutically acceptable form of histaminc for a period of time sufficient to obtain stable levels of circulating blood histamine. Preferably, the histamine is administered in multiple doses. Advantageously, the histamine is administered at a rate of from about 0.025 to 0.3 mg/minute. More advantageously, the histamine is administered at a rate of about 0.1 mg/minute. In one aspect of this preferred embodiment, the histamine is administered over a time period of between about 1 and 60 minutes, preferably over a time period of between about 1 and 30 minutes. Advantageously, the histamine is administered at a total daily dose of between about 0.4 and 10 mg; more advantageously, the histamine is administered at a total daily dose of between about 0.5 and 2 mg. preferably, the administering step is subcutaneous, intravenous, intramuscular, intraocular, oral, transdermal, intranasal or rectal.

The present invention also provides a transdermal patch comprising histamine, said patch capable of delivering an effective amount of histamine to an individual in less than about 30 minutes.

Another embodiment of the invention is a composition comprising between about 3 and 50 ml of a solution of a pharmaceutically acceptable form of histamine in a septum sealed vial. Preferably, the composition comprises between about 10 and 20 ml of the solution; more preferably, the composition comprises about 5 ml of the solution. Preferably, the concentration of histamine in the solution is between about 0.01 and 100 mg/ml. More preferably, the concentration of histamine is between about 0.1 and 50 mg/ml. Most preferably, the concentration of histamine is between about 1 and 10 mg/ml. Advantageously, the vial has a puncturable seal. Preferably, the vial is sterile. In another aspect of this preferred embodiment, the solution contains an isotonic carrier or preservative.

Other objects, advantages and features of the present invention will become apparent to those skilled in the art from the following discussion.

DETAILED DESCRIPTION OF THE PREFERRED EMBODIMENT

Figure 1:
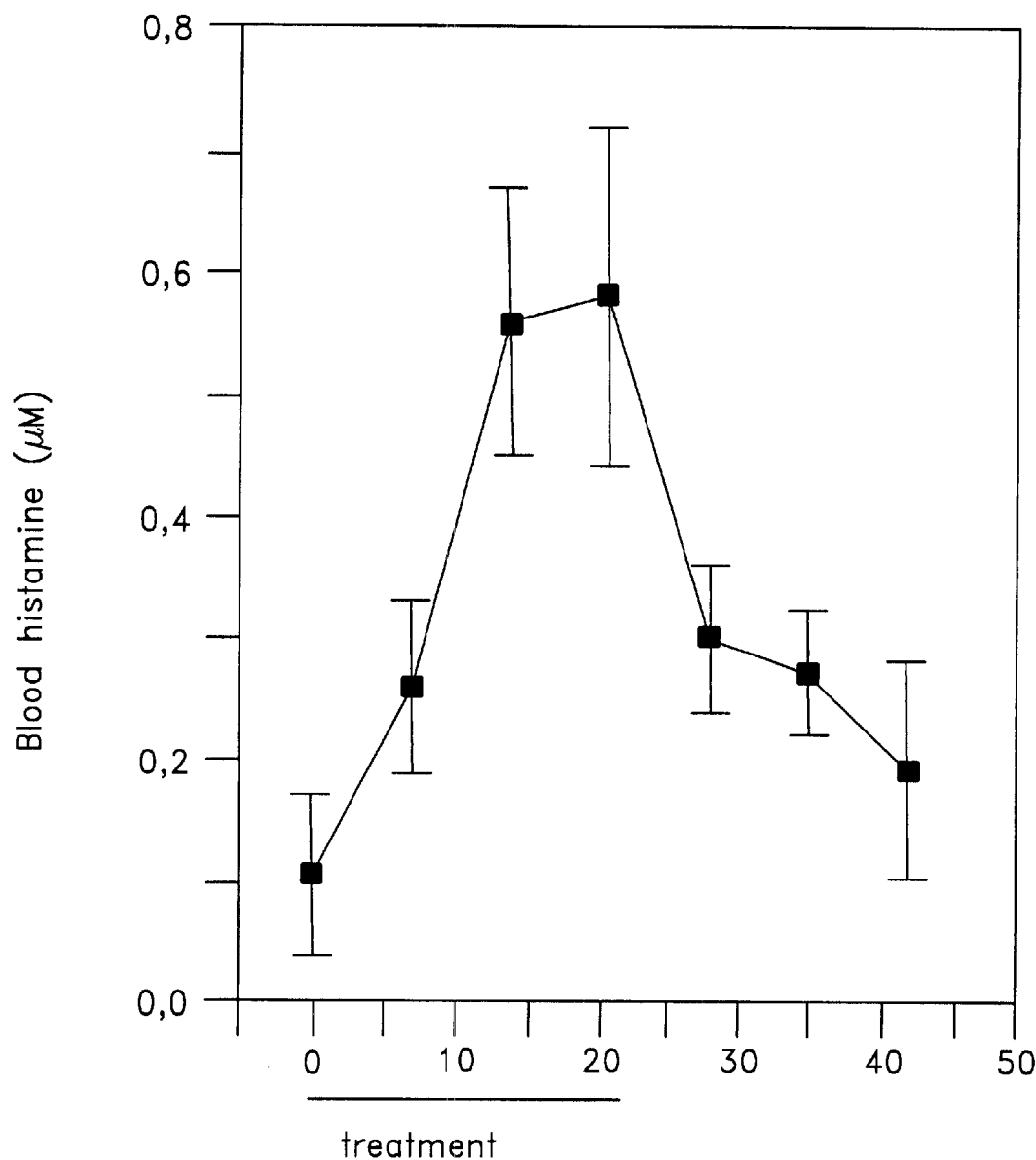
FIG. 1 shows that it is possible to obtain stable beneficial levels of circulating blood histamine.

Prior to the present invention, histamine was believed to have an extremely short half life, on the order of five minutes, in the blood. Beaven, M. A., Factors regulating availability of histamine at tissue receptors in Pharnmacology of Histamine Receptors, C. R. Ganellin and M. E. Parsons eds., Wright PSG, Bristol, U. K. pp. 103–145 (1982). The present invention arose from the unexpected finding that, contrary to the prior reports, it is possible to achieve stable levels of circulating blood histamine lasting several hours or even days from the time of histamine administration. The present invention is the first report of stable circulating blood histamine. Using regimens involving the administration of both $H_2$-receptor antagonists and histamine, Burtin was able to obtain normal levels of circulating blood histamine in cancer subjects experiencing stabilization of the disease. (Burtin et al., Eur. J. Clin. Oncol. 24: 161–167 (1988)). However, the normal levels reported by Burtin were most likely a consequence of the stabilization of the cancer rather than an observation of stable circulating levels of histamine for a significant period following administration. Evidence that the levels reported in Burtin were a consequence of physiological stabilization comes from the fact that the normal levels of histamine reported by Burtin when the subjects experienced a remission dropped to below normal levels before the subjects' deaths. Burtin did not specify the time after administration at which circulating histamine levels were measured, but it seems likely that the normal levels reported by Burtin were a consequence of endogenously produced histamine associated with stabilization of the cancer rather than an observation of persistence of extrinsically administered histamine.

Subjects suffering from cancer often exhibit decreased levels of circulating blood histamine. (Burtin et al. Decreased blood histamine levels in subjects with solid malignant tumors, Br. J. Cancer 47: 367–372 (1983)). Thus, the observation of stable and beneficial blood histamine levels lasting hours or days after histamine administration finds ready application to cancer and antiviral treatments based on synergistic effects between histamine and agents which enhance cytotoxic effector cell mediated cytotoxicity. In such protocols, the cytotoxic activity of NK cells and CTLs is enhanced by combining the administration of histamine to attain a stable level of circulating histamine sufficient to augment the activity of an agent which acts in synergy with histamine to increase cytotoxicity with the administration of the agent.

Additionally, chemotherapeutic treatments aimed at destroying the malignancy may result in lowered blood histamine levels. Example 1, below describes the decrease in blood histamine levels following treatment with the chemotherapeutic/cytostatic agents cytarabine and thioguanine. α-IFN causes a decrease in histamine levels as well.

EXAMPLE 1

In five patients with AML in remission, histamine levels in whole blood specimens were analyzed 1–5 days before and 1–2 weeks after treatment with cytarabine ($16mg/m^2$/day subcutaneously) and thioguanine (40 mg/day orally) for 21 days or until the platelet count was $\leq 50 \times 10^9/1$. Histamine was analyzed in heparinized venous blood using the radioimmunoassay available from Biomerica Inc., Newport Beach, Calif. 92663 (catalog no. 1051) according to the instructions which accompanied the assay kit.

In all patients, histamine levels declined after the treatment with cytostatics. (See Table below).

| Blood Histamine Before Patient Treatment ($\mu$moles/l) | Blood Histamine after Treatment ($\mu$moles/l) |
| --- | --- |
| 1. 0.22 | not detectable |
| 2. 0.12 | not detectable |
| 3. 0.18 | not detectable |
| 4. 0.93 | 0.38 |
| 5. 0.24 | 0.14 |

The present invention may be used to restore or maintain beneficial stable blood histamine levels in subjects whose blood histamine levels have decreased as a consequence of chemotherapy.

Beneficial levels of circulating histamine can be achieved by administering histamine before, during, or after treatment with agents which enhance natural killer cell cytotoxicity or chemotherapeutic agents.

Thus, this invention relates to a method of augmenting the activity of an agent which enhances cytotoxic effector cell cytotoxicity comprising administering histamine such that a stable blood histamine concentration sufficient to augment the cytotoxicity enhancing effect of said agent is achieved, and administering a beneficial amount of said agent, wherein the cytotoxicity enhancing effects of said agent are augmented. As used herein, "histamine" includes histamine, its dihydrochloride salt (histamine dihydrochloride), histamine diphosphate, other histamine salts, esters, or prodrugs, and $H_2$ receptor agonists. Serotonin and 5HT agonists are also contemplated. The administration of compounds which induce the release of endogenous histamine from the patient's own tissues are also included within the scope of the present invention; thus, the term "histamine" as used herein incorporates these compounds as well.

In one aspect of the present invention, the histamine is administered prior to administration of the agent which enhances NK cell and CTL cytotoxicity. In another embodiment, the histamine is administered following the administration of the agent which enhances cytotoxicity. In a fuirther embodiment, the histamine is administered during the course of administration of the agent which enhances cytotoxicity. In another embodiment, the histamine is administered prior, during, and after the administration of the agent which enhances cytotoxicity.

In one embodiment, the histamine is administered at least 1 day prior to the administration of the agent which enhances cytotoxicity. In a preferred embodiment beneficial stable levels of circulating blood histamine are obtained by administering histamine at a dosage of 0.4 to 10 mg/day. In a further preferred embodiment, the histamine is administered over a period of 1 to 4 weeks in repeated cycles up to 52 weeks. In a highly preferred embodiment, the histamine is administered for a period of 1–2 weeks repeated in cycles up to 52 weeks. In one embodiment of the invention, the beneficial stable level of circulating blood histamine concentration is at least 0.2 $\mu$mol/L.

In one embodiment of the present invention the cytotoxicity enhancing agent is at least one cytokine. Preferentially, the cytokine is interleukin-2. In a preferred aspect of the invention, the interleukin-2 is administered in an amount of 0.5–50–80 $\mu$g/kg/day. In a further preferred embodiment, the interleukin-2 is administered for a period of 1 day to 4 weeks in repeated cycles up to 12 months.

In another embodiment of the invention, the cytokine is interferon-α. Preferentially, the interferon-a is administered at a dosage of 10,000–200,000 U/kg/day. For treatment of primary melanoma, the preferred dosage of interferon-α is 200,000 U/kg/day. For treatment of other cancers, the preferred dosage of interferon-α is 50,000 U/kg/day. In a further embodiment, the interferon-a is administered for a period of up to 18 months. Preferentially, the interferon-a is administered for a period of between 2–6 weeks in repeated cycles up to 12 months.

In yet another embodiment, the cytotoxicity enhancing agent comprises interferon-α and interleukin-2.

Another aspect of the invention is a method of treating a subject having a malignancy with histamine and a second beneficial agent wherein the activity of said second beneficial agent is augmented by histamine comprising administering a pharmaceutically acceptable form of histamine such that a beneficial blood histamine level is achieved and administering said second beneficial agent.

In one embodiment of this aspect, the histamine is administered prior to the second beneficial agent. In a preferred embodiment of this aspect, the histamine is administered at least 1 day prior to the administration of the second beneficial agent.

In another embodiment of this invention, the histamine is administered after the second beneficial agent. In yet another embodiment, the histamine is administered during the course of administration of said second beneficial agent. In another aspect of the invention, the histamine is administered prior, during, and after the second beneficial agent.

Preferentially, the second beneficial agent acts to stimulate the cytotoxic activity of NK cells and CTLs.

A third aspect of the present invention is a method of enhancing the cytotoxic activity of NK cells and CTLs comprising
  a) measuring blood histamine levels in a subject to determine whether the cytotoxic activity of said subject's NK cells and CTLs could be enhanced by increasing the levels of blood histamine in said subject;
  b) administering a pharmaceutically acceptable form of histamine to a subject for whom said measuring step indicated that the cytotoxic activity of said subject's NK cells and CTLs could be enhanced by increasing said subject's blood histamine levels, such that beneficial levels of blood histamine are achieved; and
  c) administering a second agent to said subject having beneficial levels of blood histamine, such that the cytotoxic activity of said subject's NK cells and CTLs is enhanced.

In one aspect of the invention, the histamine is administered prior to the second agent. In a preferred version of this aspect, the histamine is administered at least 1 day prior to the administration of the second agent.

In another aspect of the invention, histamine is administered after the second agent. In another embodiment, histamine is administered during the administration of the second agent. In another embodiment, the histamine is administered prior, during, and after the administration of the second agent. In each instance, one embodiment of the invention includes an antiviral or antimicrobial agent as the second agent.

The present invention also includes a method of treating a malignancy comprising treating a subject having a malignancy with a chemotherapeutic agent and achieving and maintaining a beneficial stable level of circulating blood histamine by administering histamine in a dose sufficient to attain said beneficial stable levels of circulating blood histamine.

In one embodiment, the histamine is administered before the chemotherapeutic agent. In another embodiment, the histamine is administered after the chemotherapeutic agent. In another aspect of the invention, the histamine is administered during treatment with the chemotherapeutic agent. In yet another embodiment, the histamine is administered prior, during, and after treatment with the chemotherapeutic agent.

It will be appreciated that the subject's circulating blood histamine levels may be monitored during the course of treatment and boosted to beneficial levels whenever levels drop below beneficial levels or approach the lower limits of beneficial levels. For example, in this embodiment, histamine may be administered whenever the subject's histamine levels drop below 0.2 $\mu$mole/L.

Alternatively, it will be appreciated that histamine may be administered at periodic intervals at dosages sufficient to establish and maintain beneficial levels.

Routes and carrier compositions for administering histamine and cytokines have been disclosed in U.S. Pat. No. 5,348,739, which is incorporated herein by reference. Additionally, methods for administering chemotherapeutic agents are well established.

In another preferred embodiment, histamine is administered to an individual exhibiting decreased circulating blood histamine levels (i.e. lower than about 0.2 $\mu$mole/L). Such decreased histamine levels may result from, or be a contributing factor to, for example, cancer, viral infections, or other infectious agents. Monocytes and macrophages produce hydrogen peroxide which down-regulates natural killer cells and thus compromises the ability of the immune system to fight infections such as viral infections. Histamine inhibits the production of hydrogen peroxide by monocytes and macrophages. Thus, elevation of stable circulating blood histamine levels in individuals in need of such elevation is useful in stimulating the ability of the immune system to fight infections. In a preferred embodiment, beneficial stable levels of circulating blood histamine are obtained by administering histamine at a dosage of about 0.2 to 10 mg/day. In a more preferred embodiment, the histamine is administered over a period of about one to four weeks. In a highly preferred embodiment, the histamine is administered for a period of one to two weeks. The histamine may be administered for up to 12 or 18 months. Histamine may be either used alone or in conjunction with other therapeutic agents, or in preparation for the administration of other agents.

Histamine may be administered at periodic intervals at dosages sufficient to establish and maintain beneficial levels thereof. Although the dosages will vary depending on an individual's histamine levels and other factors, the dosage can be calculated using well known dose-response tests.

For the purposes of the above treatments, beneficial levels of blood histamine are at least 0.2 $\mu$mole/L.

Stable Circulating Blood Histamine Levels

As described above, the present invention is based on the observation that it is possible to obtain beneficial and stable levels of circulating blood histamine. Example 2 depicts the stable beneficial levels of circulating blood histamine obtained following histamine administration. Surprisingly, beneficial levels of circulating blood histamine persisted for considerable periods after histamine administration ceased.

EXAMPLE 2

Five patients with AML in remission received treatment with histamine dihydrochloride diluted in sterile sodium chloride purchased from Apoteksbolaget, Umea, Sweden and human recombinant interleukin-2 (Proleukin®) obtained from the commercially available vial (Eurocetus, the Netherlands). Histamine and IL-2 were administered morning and night at separate subcutaneous injection sites over a period of 21 consecutive days. The histamine was given as subcutaneous injections using 1 ml syringes containing 0.1 mg of histamine/ml. The histamine treatment was given twice daily (morning and night) at a dosage of 0.4–0.7 mg histamine per injection (i.e. a daily total dose of histamine of 0.8–1.4 mg/day).

The IL-2 was given as subcutaneous injections using separate 1-mi syringes. The IL-2 syringes contained 50 pg of IL-2/ml. The IL-2 treatment was given twice daily (morning and night), and the dose was 35–50 $\mu$g of IL-2 per injection, i.e. a daily total dose of 70–100 $\mu$g/day.

Peripheral blood venous samples were drawn in 10 ml heparinized test tubes before the onset of treatment and weekly thereafter. The samples were drawn at least 8 hours after the last injections of histamine and IL-2. The concentration of histamine in the whole blood samples was analyzed by use of a double antibody radioimmunoassay kit obtained from Biomerica, Inc., Newport Beach, Calif. 92663 (catalog no. 1051). The manufacturer's instructions provided with the kit, dated June, 1989, were followed. Blood histamine levels were measured at the indicated times.

FIG. 1 shows the results of the experiments described above. Data are given as the concentration of histamine in micromoles/lI (mean±standard error of the mean).

The subjects exhibited blood histamine levels of less than 0.2 $\mu$mole/L at the start of the experiment. Following histamine administration, circulating blood histamine levels rose to beneficial levels. Surprisingly, the circulating blood histamine levels remained elevated for sustained periods of time, even after histamine administration was discontinued.

Treatments Employing a Combination of Histamine and Interleukin-2

The stable blood histamine levels discussed above find application in treatments in which NK cell and CTL cyto-toxicity is augmented through the synergistic effects of histamine and agents which enhance cytotoxic effector cell cytotoxicity. As discussed above, one such enhancer of cytotoxicity is interleukin-2. Examples 3 and 4 describe methods of treatment in which a stable and beneficial level of histamine is achieved which augments the activity of IL-2.

EXAMPLE 3

0.5 mg/day of histamine in a pharmaceutically acceptable form is injected subcutaneously in a sterile carrier solution into subjects having a malignancy. One week later, after circulating blood histamine levels have increased to at least 0.2 $\mu$mole/L, IL-2 administration is begun. Human recombinant IL-2 (Proleukin®, Eurocetus) is administered by continuous infusion of 27 $\mu$g/kg/day on days 1–5 and 8–12.

The above procedure is repeated every 4–6 weeks until an objective regression of tumor disease is observed. The therapy may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 $\mu$mole/L, injecting 0.5 mg/day of a pharmaceutically acceptable form of histamine to restore circulating blood histamine levels above 0.2 $\mu$mole/L.

The treatment can also include periodically boosting circulating blood histamine levels by administering 0.5 mg/day histamine over a period of one to two weeks at regular intervals, such as biweekly, in order to maintain circulating blood histamine levels above 0.2 $\mu$mole/L.

EXAMPLE 4

Human recombinant IL-2 (Proleukin®, Eurocetus) is administered by continuous infusion of 27 $\mu$g/kg/day on days 1–5 and 8–12 into patients infected with herpes simplex virus (HSV) type 2. 0.5 mg/day of histamine in a pharmaceutically acceptable form is injected subcutaneously in a sterile carrier solution until circulating blood histamine levels have increased to at least 0.2 $\mu$mole/L.

The above procedure is repeated every 4–6 weeks until an objective regression of the disease is observed. The therapy may be continued even after a partial or complete response has been observed.

The treatment can additionally include monitoring circulating levels of blood histamine periodically and, when circulating histamine levels drop below 0.2 $\mu$mole/L, injecting 0.5 mg/day of a pharmaceutically acceptable form of histamine to restore circulating blood histamine levels above 0.2 $\mu$mole/L.

The treatment can also include periodically boosting circulating blood histamine levels by administering 0.5 mg/day histamine over a period of one to two weeks at regular intervals, such as bi-weekly, in order to maintain circulating blood histamine levels above 0.2 $\mu$mole/L.

If desired, 0.5 mg/day of histamine in a pharmaceutically acceptable form can also be injected subcutaneously for about one week prior to the start of treatment with IL-2, in order to increase circulating blood histamine levels to at least 0.2 $\mu$mole/L.

Combination of Histamine and Interferon-$\alpha$

Another enhancer of NK cell cytotoxicity is interferon-$\alpha$. Example 5 describes methods of treatment in which a stable and beneficial level of histamine is achieved which augments the activity of interferon-α.

EXAMPLE 5

0.5 mg/day of histamine in a pharmaceutically acceptable form is injected subcutaneously in a sterile carrier solution into subjects having a malignancy or who have had a primary tumor surgically removed. One week later, after circulating blood histamine levels have increased to at least 0.2 μmole/L, interferon-α administration is begun. Interferon is administered in doses of 50,000 U/kg/day in a suitable carrier solution for 2–6 weeks.

The above procedure is repeated 3 times a week, or even several times daily, for up to 24 months until an objective regression of the tumor is observed. The therapy with histamine, IL-2 and interferon may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 μmole/L, injecting an additional 0.5–2.0 mg/day of a pharmaceutically acceptable form of histamine to restore circulating blood histamine levels above 0.2 μmole/L .

The treatment can also include periodically boosting circulating blood histamine levels by administering 0.5 mg/day histamine over a period of one to two weeks at regular intervals, such as bi-weekly, in order to maintain circulating blood histamine levels above 0.2 μmole/L.

Additionally, the frequency of interferon-α administration may be varied depending on the patient's tolerance of the treatment and the success of the treatment. For example, interferon may be administered three times per week, or even daily, for a period of up to 24 months. Those skilled in the art are familiar varying interferon treatments to achieve both beneficial results and patient comfort.

Example 6 describes methods of treatment in which a stable and beneficial level of histamine is achieved which augments the activity of interferon-α in antiviral therapies.

EXAMPLE 6

0.5 mg/day of histamine in a pharmaceutically acceptable form is injected subcutaneously together with interferon-α in patients infected with hepatitis C. 0.5–2.0 mg/day histamine is administered in order to maintain circulating blood histamine levels above 0.2 μmole/L. Interferon is administered in doses of 50,000 U/kg/day in a suitable carrier solution.

The above procedure is repeated 3 times a week, or even several times daily, for up to 24 months until nonnalized liver enzymes and clearance of viral RNA from serum is observed. The therapy with histamine and interferon may be continued even after a partial or complete response has been observed.

The treatment can additionally include monitoring circulating levels of blood histamine periodically and, when circulating histamine levels drop below 0.2 μmole/L, injecting an additional 0.5–2.0 mg/day of a pharmaceutically acceptable form of histamine to restore circulating blood histamine levels above 0.2 μmole/L.

The treatment can also include periodically boosting circulating blood histamine levels by administering 0.5–2.0 mg/day histamine over a period of one to two weeks at regular intervals, such as bi-weekly, in order to maintain circulating blood histamine levels above 0.2 μmole/L.

0.5 mg/day of histamine in a pharmaceutically acceptable form can also be injected subcutaneously for about one week prior to the start of treatment with interferon, in order to increase circulating blood histamine levels to at least 0.2 μmole/L.

Additionally, the frequency of interferon-α administration may be varied depending on the patient's tolerance of the treatment and the success of the treatment. For example, interferon may be administered three times per week, or even daily, for a period of up to 24 months. Those skilled in the art are familiar varying interferon treatments to achieve both beneficial results and patient comfort.

Combination of Histamine, IL-2 and Interferon-α

Beneficial stable levels of circulating blood histamine can also be employed in conjunction with treatments involving several enhancers of NK cell cytotoxicity. Example 7 describes how to administer such treatments.

EXAMPLE 7

Subjects having a malignancy or viral infection such as hepatitis B, hepatitis C, human immunodeficiency virus (HIV), human papilloma virus (HPV) or herpes simplex virus (HSV) type 1 or 2 are administered human recombinant IL-2 (Proleukin®, Eurocetus) by continuous infusion of 27 μg/kg/day on days 1–5 and 8–12. Additionally, subjects also receive a daily dose of $6 \times 10^6$ U interferon-α administered by subcutaneous injection, and 0.5–2.0 mg/day of a pharmaceutically acceptable form of histamine. Histamine is administered for a period of one to two weeks until circulating blood histamine levels reach above 0.2 μmole/L.

The above procedure is repeated every 4–6 weeks until an objective regression of the tumor is observed, or until improvement in the viral infection occurs. The therapy may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 μmole/L, injecting 0.5–2.0 mg/day of a pharmaceutically acceptable form of histamine for a period of one to two weeks to restore circulating blood histamine levels above 0.2 μmole/L.

The treatment can also include periodically boosting circulating blood histamine levels by administering histamine at regular intervals, such as daily, bi-weekly or weekly.

Histamine in a pharmaceutically acceptable form, such as a sterile carrier solution, can be injected subcutaneously 0.5–1.0 mg/injection, 1–4 times per day, for about one week prior to the start of treatment with IL-2 and interferon, in order to increase circulating blood histamine levels to at least 0.2 μmole/L.

Additionally, the frequency of interferon-α administration may be varied depending on the patient's tolerance of the treatment and the success of the treatment. For example, interferon may be administered three times per week, or even daily, for a period of up to 24 months. Those skilled in the art are familiar varying interferon treatments to achieve both beneficial results and patient comfort.

Combination of Histamine and Chemotherapeutic Agents

Histamine may also be used in conjunction with chemotherapeutic agents. Typically, levels of circulating histamine decline during chemotherapy. Low levels of circulating histamine may result in the suppression of NK cell cytotoxicity by monocytes. This monocyte mediated suppression may be eliminated by administration of histamine prior, during, following or throughout chemotherapy in order to return circulating histamine levels to normal.

Accordingly, the present invention contemplates the restoration of circulating blood histamine levels to normal levels in conjunction with chemotherapeutic agents. Additionally, the treatment may also include administration of IL-2 and/or interferon-α.

Representative compounds used in cancer therapy include cyclophosphamide, chlorambucil, melphalan, estramustine, iphosphamide, prednimustin, busulphan, tiottepa, carmustin, lomustine, methotrexate, azatlioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amacnne, mitoxantron, tamoxifen, nilutamid, and aminoglutemide. Procedures for employing these compounds against malignancies are well established. In addition, other canccr therapy compounds may also be utilized in the present invention.

Malignancies against which the treatment may be directed include, but are not limited to, primary and metastatic malignant tumor disease, hematological malignancies such as acute and chronic myelogenous leukemia, acute and chronic lymphatic leukemia, multiple myeloma, Waldenstroms Macroglobulinemia, hairy cell leukemia, myelodysplastic syndrome, polycytaemia vera, and essential thrombocytosis.

As described above, histamine+IL-2 has proven an effective combination with traditional chemotherapeutic methods in treating acute myelogenous leukemia. (Brune and Hellstrand, Br. J. Haematology, March 1996). Procedures for using the present invention in combination with chemotherapeutic agents and IL-2 are presented in Example 8. It will be appreciated that beneficial stable levels of circulating histamine may also be employed in treatments using only chemotherapeutic agents.

EXAMPLE 8

Subjects with AML in first, second, subsequent or complete remission are treated in 21-day courses with IL-2 [35–50 μg (equivalent to 6.3–9×10$^5$ IU) s.c. twice daily], repeated with six-week intermissions and continued until relapse. In cycle #1, patients receive three weeks of low dose chemotherapy consisting of 16 mg/im2/day cytarabine, and 40 mg/day thioguanine. Thereafter, patients are injected subcutaneously with 0.5 mg/day of a pharmaceutically acceptable form of histamine for a period of 1 week to boost circulating histamine to a stable beneficial level above 0.2 μmole/L. Thereafter, patients receive 100 μg of interleukin-2/day for three weeks. Circulating histamine levels are boosted to beneficial levels by administering 0.5 mg/day of a pharmaceutically acceptable form of histamine during the second week of this period. Thereafter, the subjects are allowed to rest for one to six weeks.

After the rest period at the end of cycle 1, cycle #2 is initiated. 0.5 mg/injection twice a day of a pharmaceutically acceptable form of histamine in a sterile carrier solution is injected subcutaneously until circulating blood histamine levels of at least 0.2 μmole/L are achieved. Cytarabine (16 mg/m$^2$/day s.c.) and thioguanine (40 mg/day orally) are given for 21 days (or until the platelet count is ≦50×10$_9$/1). In the middle week, patients receive 0.5 mg/injection twice per day of a pharmaceutically acceptable form of histamine to boost circulating histamine to beneficial levels. At the end of the three week chemotherapy treatment, patients receive 0.5 mg/injection twice per day of a pharmaceutically acceptable form of histamine for a week. Thereafter, patients receive 100 μg/day of interleukin-2 for three weeks. Circulating histamine levels are boosted in the middle week of the three week IL-2 treatment as described above. Patients are permitted to rest for two to six weeks.

Thereafter, cycle #3 is initiated. Cycle #3 is identical to cycle #2.

Alternatively, circulating histamine levels may be periodically monitored throughout the above procedure and histamine may be administered whenever circulating levels drop below a desirable level in order to maintain a beneficial level of blood histamine above 0.2 μmole\L. Additionally, histamine may be administered at regular intervals during the treatment to maintain beneficial circulating levels. Another alternative is to provide histamine in a depot or controlled release form.

EXAMPLE 9

Subjects having low circulating blood histamine levels (i.e. 0.2 μM or less) associated with, for example, a malignancy or viral infection such as hepatitis B, hepatitis C, human immunodeficiency virus (HIV), human papilloma virus (HPV) or herpes simplex virus (HSV) type 1 or 2 are administered 0.2–2.0 mg/day of a pharmaceutically acceptable form of histamine. Histamine is administered for a period of one to two weeks until circulating blood histamine levels are above 0.2 μmole/L.

The above procedure is repeated every 4–6 weeks until an objective regression of the tumor is observed, or until improvement in the viral infection occurs. The therapy may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 μmole/L, injecting 0.2–2.0 mg/day of a pharmaceutically acceptable form of histamine for a period of one to two weeks to restore circulating blood histamine levels above 0.2 μmole/L.

The treatment can also include periodically boosting circulating blood histamine levels by administering histamine at regular intervals, such as daily, biweekly or weekly.

Histamine in a pharmaceutically acceptable form, such as a sterile carrier solution, can be injected subcutaneously 0.5–1.0 mg/injection, 1–4 time per day in order to increase circulating blood histamine levels to at least 0.2 μmole/L.

Optimizing Delivery of Histamine

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include tablets, capsules, gels, microspheres, liposomes, ocular inserts, minipumps, and other infusion devices such as pumps and syringes. Implantable or injectable polymer matrices, and transdermal formulations, from which active ingredients are slowly released are also well known and can be used in the present invention.

Suitable infusion devices for use in the present invention include syringe pumps, auto injector systems and minipumps. Exemplary devices include the Ambulatory Infusion Pump Drive, Model 30, available from Microject Corp., Salt Lake City, Utah, and the Baxa Syringe Infuser, available from Baxa Corporation, Englewood, Colo. Any device capable of delivering histamine in the manner described below can be used in the methods of the present invention.

The infusion devices of the present invention preferably have an effective amount of histamine, histamine dihydrochloride, histamine phosphate, serotonin, a 5HT agonist, an $H_2$ receptor agonist or a substance which induces the release of an effective therapeutic amount of endogenous histamine contained therein. The device can be pre-loaded with the desired substance during manufacture, or the device can be filled with the substance just prior to use. Pre-filled infusion pumps and syringe pumps are well known to those of skill in the art. The active substance can be part of a formulation which includes a controlled release carrier, if desired. A controller is used with the device to control the rate of administration and the amount of substance to be administered. The controller can be integral with the device or it can be a separate entity. It can be pre-set during manufacture, or set by the user just prior to use. Such controllers and their use with infusion devices are well known to those of skill in the art.

Controlled release oral formulations are also well known. Active compound is incorporated into a soluble or erodible matrix. Hydrophilic gums, such as hydroxymethylcellulose, are commonly used. A lubricating agent such as magnesium stearate, stearic acid, or calcium stearate can be used to aid in the tableting process.

For the purpose of parenteral administration, histamine or compounds which induce endogenous histamine release can be combined with distilled water, preferably buffered to an appropriate pH and having appropriate (e.g., isotonic) salt concentrations. Histamine formulations can be provided as a liquid or as a powder which is reconstituted before use. They can be provided as prepackaged vials, syringes, or injector systems.

Histamine may also be provided in septum-sealed vials in volumes ranging from about 3 to 50 ml for administration to an individual in need of elevated circulating blood histamine levels. In a preferred embodiment, the vials contain volumes of 3, 5, 6, 8, 10 and 20 ml. The vials are preferably sterile. The vials may optionally contain an isotonic carrier medium and/or a preservative. Any desired amount of histamine may be used to give a desired final histamine concentration. In a preferred embodiment, the histamine concentration is between about 0.01 mg/ml and 100 mg/ml. More preferably, the histamine concentration is between about 0.1 and 50 mg/ml. Most preferably, the histamine concentration is between about 1 mg/ml and 10 mg/ml. At the lower end of the volume range, it is preferred that individual doses are administered, while at the higher end it is preferred that multiple doses are administered.

Controlled release preparations can be achieved by the use of polymers to complex or absorb the histamine. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

Hydrogels, wherein the histamine compound is dissolved in an aqueous constituent to gradually release over time, can be prepared by copolymerization of hydrophilic mono-olefinic monomers such as ethylene glycol methacrylate. Matrix devices, wherein the histamine is dispersed in a matrix of carrier material, can be used. The carrier can be porous, non-porous, solid, semi-solid, permeable or impermeable. Alternatively, a device comprising a central reservoir of histamine surrounded by a rate controlling membrane can be used to control the release of histamine. Rate controlling membranes include ethylene-vinyl acetate copolymer or butylene terephthalate/polytetramethylene ether terephthalate. Use of silicon rubber depots are also contemplated.

In a preferred embodiment, transdermal patches, steady state reservoirs sandwiched between an impervious backing and a membrane face, and transdermal formulations, can also be used to deliver histamine and histamine agonists. Transdermal administration systems are well known in the art. Occlusive transdermal patches for the administration of an active agent to the skin or mucosa are described in U.S. Pat. Nos. 4,573,996, 4,597,961 and 4,839,174, which are hereby incorporated by reference. One type of transdermal patch is a polymer matrix in which the active agent is dissolved in a polymer matrix through which the active ingredient diffuises to the skin. Such transdermal patches are disclosed in U.S. Pat. Nos. 4,839,174, 4,908,213 and 4,943,435, which are hereby incorporated by reference.

Present transdennal patch systems are designed to deliver smaller doses over longer periods of time, up to days and weeks, whereas the present invention would specifically deliver an effective dose of histamine in a range of between about 2 and 60 minutes, depending upon the dose, with a preferred dose being delivered within about 30 minutes. These patches allow rapid and controlled delivery of histamine. A rate-controlling outer microporous membrane, or micropockets of histamine dispersed throughout a silicone polymer matrix, can be used to control the release rate. Such rate-controlling means are described in U.S. Pat. No. 5,676,969, which is hereby incorporated by reference. In another preferred embodiment, the histamine is released from the patch into the skin of the patient in about 30 minutes or less. In a preferred embodiment, the histamine is released from the patch at a rate of between about 0.025 mg to 0.3 mg per minute for a dose of between about 0.2 mg and 3 mg per patch. In a more preferred embodiment, the patch contains between about 0.7 and 1.5 mg.

These transdermal patches and formulations can be used with or without use of a penetration enhancer such as dimethylsulfoxide (DMSO), combinations of sucrose fatty acid esters with a sulfoxide or phosphoric oxide, eugenol or Azone. The use of electrolytic transdermal patches is also within the scope of the present invention. Electrolytic transdermnal patches are described in U.S. Pat. Nos. 5,474,527, 5,336,168, and 5,328,454, the entire contents of which are hereby incorporated by reference.

Another possible method to control the release of histamine is to incorporate the histamine into particles of a polymeric material such as polyesters, polyamino acids, hydrogels, poly lactic acid, or ethylene vinylacetate copolymers.

Alternatively, instead of incorporating histamine into these polymeric particles, it is possible to entrap the histamine in microcapsules prepared, for example, by coacervation techniques, or by interfacial polymerization, for example hydroxymethylcellulose or gelatin-microcapsules, respectively, or in colloidal drug delivery systems, for example, liposomes, albumin microspheres, microemulsions, nanoparticles, and nanocapsules, or in macroemulsions. Such technology is well known to those of ordinary skill in pharmaceutical sciences.

Preferably, the histamine is injected, infused, or released into the patient at a rate of from about 0.025 to 0.2 mg/min. A rate of about 0. 1 mg/min is preferred. The histamine is preferably administered over a period of time ranging from about 1, 3 or 5 minutes to about 30 minutes, with an upper limit of about 20 minutes being preferred, such that the total daily adult dose of histamine ranges from between about 0.4 to about 10.0 mg, with about 0.5 to about 2.0 mg being preferred. Histamine administered over longer periods of time, i.e., longer than about 30 minutes, has been found to result in decreased or lack of efficacy, while rapid administration over less than 1–3 minutes can cause more pronounced and serious side effects, which include anaphylaxis, heart failure, bronchospasm, pronounced flushing, discomfort, increased heart rate and respiratory rate, hypotension, and severe headache.

Administration of each dose of histamine can occur from once a day to up to about four times a day, with twice a day being preferred. Administration can be subcutaneous, intravenous, intramuscular, intraocular, oral, transdermal, intranasal, or rectal and can utilize direct hypodermic or other injection or infusion means, or can be mediated by a controlled release mechanism of the type disclosed above. Any controlled release vehicle or infusion device capable of administering a therapeutically effective amount of histamine over a period of time ranging from about 1 to about 30 minutes can be used. In a preferred embodiment, intranasal delivery is accomplished by using a solution of histamine in an atomizer or nebulizer to produce a fine mist which is introduced into the nostrils. For rectal delivery, histamine is formulated into a suppository using methods well known in the art.

In addition to histamine, histamine dihydrochloride, histamine phosphate, other histamine salts, esters, congeners, prodrugs, and $H_2$ receptor agonists, the use of serotonin, 5HT agonists, and compounds which induce release of histamine from the patient's own tissues is also included within the scope of the present invention. Retinoic acid, other retinoids such as 9-cis-retinoic acid and all-trans-retinoic acid, IL-3 and ingestible allergens are compounds which are known to induce the release of endogenous histamine. These compounds can be administered to the patient by oral, intravenous, intramuscular, subcutaneous, and other approved routes. However, the rate of administration should result in a release of endogenous histamine in the rage of from about 0.05–2.0 mg/min.

Administration of each dose of a compound which induces histamine release can occur from once per day to up to about four times a day, with twice per day being preferred. Administration can be subcutaneous, intravenous, intramuscular, intraocular, oral, or transdermal, and can incorporate a controlled release mechanism of the type disclosed above. Any controlled release vehicle capable of administering a therapeutically effective amount of a compound which induces histamine release over a period of time ranging from about one to about thirty minutes can be used.

What is claimed is:

1. A transdermal patch to systemically deliver an effective dose of histamine, comprising:
the effective dose of histamine and a controlled release preparation formulated in said transdermal patch to release the effective dose, of histamine over a period of time sufficient to obtain stable elevated levels of circulating blood histamine, wherein the effective dose of histamine is released at a total daily dose of between about 0.2 and 3 mg, and wherein the controlled release preparation comprises a macromolecule selected from the group consisting of polyesters, polyamino acids, polyvinylpyrrolidonie, ethylenevinyl acetate, and protamine sulfate.

2. The transdermal patch of claim 1, wherein the patch is an occlusive dermal patch.

3. The transdermal patch of claim 1, wherein the patch is a non-occlusive patch.

4. The transdermal patch of claim 1, wherein the patch releases the effective dose at a rate of between about 0.025 mg to 0.3 mg per minute.

5. The transdermal patch of claim 1, wherein the patch releases the effective dose at a rate of between a bout 0.7 mg to 1.5 mg per minute.

6. The transdermal patch of claim 1, wherein the patch releases the effective dose at a rate of between about 0.25 mg to 3 mg per minute.

7. The transdermal patch of claim 1, wherein the patch releases the effective dose at a rate of about 0.5 mg/day.

8. The transdermal patch of claim 1, further comprising a chemotherapeutic agent.

9. The transdermal patch of claim 1, wherein the histamine compound is in the form of a histamine salt.

10. The transdermal patch of claim 9, wherein the histamine salt is histamine dihydrochloride.

11. The transdermal patch of claim 9, wherein the histamine salt is histamine diphosphate.

12. The transdermal patch of claim 1, wherein the histamine compound is in the form a histamine ester.

13. The transdermal patch of claim 1, wherein the histamine compound is in the form a histamine prodrug.

14. The transdermal patch of claim 1, further comprising a penetration enhancer.

15. The transdermal patch of claim 14, wherein the penetration enhancer is selected from the group consisting of dimiethylsulfoxide (DMSO) and eugenol.

16. The transdermal patch of claim 1, wherein said effective dose of histamine is released at a rate of from about 0.025 to 0.3 mg/minute.

17. The transdermal patch of claim 1, wherein said effective dose of histamine is released at a rate of about 0.1 mg/minute.

18. The transdermal patch of claim 1, wherein said effective dose of histamine is released over a time period of between about 2 and 60 minutes.

19. The transdermal patch of claim 1, wherein said effective dose of histamine is released over a time period of between about 2 and 30 minutes.

20. The transdermal patch of claim 1, further comprising an effective amount of an NK cell cytotoxicity enhancing agent.

21. The transdermal patch of claim 16, wherein the effective amount of an NK cell cytotoxicity enhancing agent is 0.5 to 80 µg/kg/day of interleukin-2.

22. The transdermal patch of claim 16, wherein the effective amount of an NK cell cytotoxicity enhancing agent is 10,000–200,000 U/kg/day of interferon-alpha.

* * * * *